(12) United States Patent
Maier et al.

(10) Patent No.: US 8,078,268 B2
(45) Date of Patent: *Dec. 13, 2011

(54) SYSTEM AND METHOD OF CHEMICAL IMAGING USING PULSED LASER EXCITATION AND TIME-GATED DETECTION TO DETERMINE TISSUE MARGINS DURING SURGERY

(75) Inventors: John S. Maier, Pittsburgh, PA (US); Shona Stewart, Pittsburgh, PA (US); Jeffrey Cohen, Pittsburgh, PA (US); Matthew Nelson, Harrison City, PA (US); Patrick J Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/565,279

(22) Filed: Sep. 23, 2009

(65) Prior Publication Data

US 2010/0081127 A1    Apr. 1, 2010

Related U.S. Application Data

(63) Continuation-in-part of application No. 11/361,256, filed on Feb. 24, 2006, now Pat. No. 7,596,404, and a continuation of application No. 10/184,580, filed on Jun. 28, 2002, now Pat. No. 6,965,793, and a continuation of application No. 10/185,090, filed on Jun. 28, 2002, now Pat. No. 6,954,667.

(60) Provisional application No. 60/656,057, filed on Feb. 24, 2005, provisional application No. 60/301,708, filed on Jun. 28, 2001, provisional application No. 61/199,236, filed on Nov. 14, 2008.

(51) Int. Cl.
*A61B 6/00* (2006.01)

(52) U.S. Cl. .......................... 600/476; 600/477; 600/473
(58) Field of Classification Search .................. 600/477, 600/476, 473
See application file for complete search history.

(56) References Cited

U.S. PATENT DOCUMENTS

| 5,105,457 | A | | 4/1992 | Glassman |
| 5,194,912 | A | | 3/1993 | Batchelder |
| 5,261,410 | A | * | 11/1993 | Alfano et al. ................. 600/475 |

(Continued)

FOREIGN PATENT DOCUMENTS

WO    PCT/US06/06663    8/2006

OTHER PUBLICATIONS

Storrie-Lombardi et al, "Hollow Cathode Ion Lasers for Deep Ultraviolet Raman Spectroscopy and Fluorescence Imaging." Review of Scientific Instruments, vol. 72, No. 12. Dec. 1, 2001.

(Continued)

*Primary Examiner* — Long V. Le
*Assistant Examiner* — Helene Bor

(57) ABSTRACT

System and method for differentiating tissue margins in a biological sample using pulsed laser excitation and time-gated detection. A region containing a biological tissue is irradiated with substantially monochromatic pulsed laser light to thereby produce Raman scattered photons. The Raman scattered photons are detected using time-gated detection to thereby obtain a Raman spectroscopic image from the irradiated region characteristic of either a neoplastic portion or a non-neoplastic portion of the region containing the biological tissue. A boundary between a neoplastic portion and a non-neoplastic portion is differentiated and the boundary location in the Raman spectroscopic image is displayed.

26 Claims, 10 Drawing Sheets

U.S. PATENT DOCUMENTS

| | | | |
|---|---|---|---|
| 5,293,872 A | 3/1994 | Alfano | |
| 5,377,004 A | 12/1994 | Owen | |
| 5,442,430 A | 8/1995 | Ishii | |
| 5,442,438 A | 8/1995 | Batchelder | |
| 5,452,723 A | 9/1995 | Wu | |
| 5,528,393 A | 6/1996 | Sharp | |
| 5,539,517 A | 7/1996 | Cabib | |
| 5,596,992 A | 1/1997 | Haaland | |
| 5,623,342 A | 4/1997 | Baldwin | |
| 5,689,333 A | 11/1997 | Batchelder | |
| 5,710,626 A | 1/1998 | O'Rourke | |
| 5,733,739 A * | 3/1998 | Zakim et al. | 435/29 |
| 5,769,081 A | 6/1998 | Alfano | |
| 5,799,656 A | 9/1998 | Alfano | |
| 5,862,273 A | 1/1999 | Pelletier | |
| 5,891,619 A | 4/1999 | Zakim | |
| 5,901,261 A | 5/1999 | Wach | |
| 5,911,017 A | 6/1999 | Wach | |
| 6,002,476 A * | 12/1999 | Treado | 356/301 |
| 6,151,522 A | 11/2000 | Alfano | |
| 6,167,287 A | 12/2000 | Chozui | |
| 6,167,297 A | 12/2000 | Benaron | |
| 6,205,354 B1 | 3/2001 | Gellermann | |
| 6,485,413 B1 | 11/2002 | Boppart | |
| 6,571,118 B1 | 5/2003 | Utzinger | |
| 6,640,132 B1 | 10/2003 | Freeman | |
| 6,665,556 B1 | 12/2003 | Alfano | |
| 6,741,884 B1 | 5/2004 | Freeman | |
| 6,748,259 B1 | 6/2004 | Benaron | |
| 6,937,885 B1 | 8/2005 | Lewis | |
| 7,039,452 B2 | 5/2006 | McClane | |
| 7,515,952 B2 | 4/2009 | Balas | |
| 2001/0052979 A1 | 12/2001 | Treado | |
| 2001/0055462 A1 | 12/2001 | Seibel | |
| 2002/0007123 A1* | 1/2002 | Balas | 600/476 |
| 2002/0113210 A1 | 8/2002 | Treado | |
| 2003/0004419 A1 | 1/2003 | Treado | |
| 2003/0114762 A1 | 6/2003 | Balas | |
| 2003/0130579 A1 | 7/2003 | McClane | |
| 2004/0038320 A1* | 2/2004 | Banerjee | 435/7.23 |
| 2004/0068193 A1 | 4/2004 | Barnes | |
| 2004/0152992 A1 | 8/2004 | Zeng | |
| 2005/0240107 A1 | 10/2005 | Alfano | |
| 2006/0013454 A1* | 1/2006 | Flewelling et al. | 382/128 |
| 2006/0155195 A1 | 7/2006 | Maier | |
| 2006/0250613 A1* | 11/2006 | Demuth et al. | 356/301 |
| 2006/0253261 A1 | 11/2006 | Maier | |
| 2006/0269972 A1 | 11/2006 | Smith | |
| 2006/0281068 A1 | 12/2006 | Maier | |
| 2007/0093708 A1 | 4/2007 | Benaron | |

OTHER PUBLICATIONS

Uzunmajakava et al, "Combined Raman and Continuous-Wave Excited Two-Photon Fluorescence Cell Imaging," Optics Letters Opt. Soc. America USA, vol. 28, No. 21. Nov. 1, 2003.

Morris et al, "Imaging Spectrometers for Fluorescence and Raman Microscopy: Acousto-Optic and Liquid Crystal Tunable Filters," Applied Spectrscopy, vol. 48, No. 7, Jul. 1994.

Morris et al, "Fluorescence and Raman Chemical Imaging of Thermoplastic Olefin (TPO) Adhesion Promotion," Langumuir 1998, vol. 14, No. 9.

European Search Report, PCT/US2005/023705, Nov. 6, 2009.

Sajid et al, "Fourier Transform Vibrational Spectroscopic Analysis of Human Cerebral Tissue," Journal of Raman Spectroscopy (1997) pp. 165-169, vol. 28.

Boppart et al, "Optical Coherence Tomography for Neurological Imaging of Human Intracortical melanoma." Neurosurgery (1998) pp. 834-841, vol. 43.

Haka et al, "Identifying Microcalicifications in Benign and Malignant Breast Lesions by Probing Differences in Their Chemical Composition Using Raman Spectroscopy," Cancer Research (2002) pp. 5375-5380, vol. 62.

Hanlon et al, "Prospects for In Vivo Raman Spectroscopy," Phy. Med. Biol. (2000) pp. R1-R59, vol. 45.

Lakshmi et al, "Tisue Raman Spectroscopy for the Study of Radiation Damage: Brain Irradiation of Mice," Radiation Research (2002) pp. 175-182, vol. 157.

Liu et al, "Near-IR Fourier Transform Raman Spectroscopy of Normal and Atherosclerotic Human Aorta," Lasers in Life Science (1992) pp. 257-264, vol. 4.

Miura et al, "Binding Mode of Congo Red to Alzheimer's Amyloid B-peptide Studied by UV Raman Spectroscopy," Journal of Raman Spectroscopy (2002) pp. 530-535, vol. 33.

Mizuno et al, "Near Infrared FT-Raman Spectra of the Rat Brian Tissues," Neuorscience Letters (1992) pp. 47-52. vol. 141.

Mizuno et al, "Near infrared Fourier Transform Raman Spectroscopic Study Human Brain—Tissues and Tumors," Journal of Raman Spectroscopy (1994) pp. 25-29, vol. 25.

Naumann, D, "FT-Infrared and FT-Raman Spectroscopy in Biomedical Research," Applied Spectroscopy Reviews (2001) pp. 239-289 vol. 36.

Petrich, W., "Mid-Infrared and Raman Spectroscopy for Medical Diagnostics," Applied Spectroscopy Reviews (2001) pp. 181-237, vol. 36.

Chandler et al, "Intraoperative Use of Real Time Ultrasonography in Neurosurgery," J Neuorsurg (1982) pp. 157-163, vol. 57.

Poon et al, "Laser-induced Fluorescence : Experimental Intraoperative Delineation of tumor Resection Margins," J. Neurosurg (1992) pp. 679-686 vol. 76.

Hansen et al, "Indocyanine Green (ICG) Staining an dDemarcation of Tumor Margins in a Rat Glloma Model," Surgical Neurol. (1993) pp. 451-456, vol. 40.

Haglund et al, "Enhanced Optical Imaging of Rat Gilomas and Tumor Margins," Neurosurgery (1994) pp. 930-941 vol. 35 No. 5.

Yuan et al, "Isolation of Cancer Stem Cells from Audit Glioblastoma Multiforme," Oncogene (2004) pp. 9392-9400, vol. 23.

Ahmad, K. "Small Subsets of Cells Initiate Brain Tumors," Lancet Oncology (2005), pp. 9, vol. 6.

Dirks, P.B. "Brain Tumor Stem Cells," Biology of Blood Marrow Transplantation, (2005) pp. 12-13, vol. 11.

Bakker Schut et al, "Real Time Tissue Characterization on the Basis of In Vivo Raman Spectra," Journal of Raman Spectroscopy, 2002, pp. 580-585 vol. 33.

Dong et al, Metal Binding and Oxidation of Amyloid-B Within Isolated Senile Plaque Cores: Raman Microscopic Evidence, Biochemicstry (2003), pp. 2768-2773, vol. 42.

Frank et al, "Characterization of Human Breast Biopsy Specimens with Near IR Raman Spectroscopy," Analytical Chemistry (1994) pp. 319-326, vol. 66.

Talbot et al, "Appliction of Fluorescence Lifetime and Hyperspectral Imaging to Tissue Autofluorescence: Arthritis," European Conference on Biomedical Optics (ECBO), Conference Paper, Jun. 12, 2005.

Goodship, A.E. et al., Kerr-Gated Picosecond Spectroscopy and Raman Photon Migration of Equine Bone Tissue, Central Laser Facility Annual Report, 2003/2004, pp. 129-130.

Treado, Patrick J., Chemical Imaging Reveals More than Microscope, Laser Focus World, 10438092, Oct. 1995, vol. 31, Issue 10, pp. 76-81.

Cederquist, Sally C., Laser-Raman Provides a View of Microfossils, Laser Focus World, 07402511, Jun. 2001, vol. 37, Issue 6, pp. 26-28.

PCT/US2006/06663, Written Opinion, mailed on Feb. 13, 2008.

CT/US2006/06663, Search Report, mailed on Feb. 13, 2008.

CT/US2006/06663, International Preliminary Report on Patentability.

* cited by examiner

| Specifications | Value | |
|---|---|---|
| Type: | Raman for Blue/Green/Red excitation | |
| Tunable Range: | 445 nm -740 nm (-3675 cm⁻¹ to 5283 cm⁻¹ for 532 nm excitation) | |
| FWHM: | 0.42 nm (13.6 cm⁻¹) | |
| Polarized Transmission: | 25±5% | @ 550nm |
| | 28±5% | @ 550nm |
| | 30±5% | @ 550nm |
| Angle of acceptance: | ±3° | |
| Tuning accuracy: | ± 1/8 FWHM | |
| Operation temperature: | +15°C to 40°C | |

SYSTEM AND METHOD OF CHEMICAL IMAGING USING PULSED LASER EXCITATION AND TIME-GATED DETECTION TO DETERMINE TISSUE MARGINS DURING SURGERY

RELATED APPLICATIONS

This application is a continuation-in-part of U.S. patent application Ser. No. 11/361,256, entitled "Method of Chemical Imaging to Determine Tissue Margins During Surgery", now U.S. Pat. No. 7,596,404, filed on Feb. 24, 2006, which is a continuation-in-part of U.S. application Ser. No. 11/204,196, filed on Aug. 9, 2005, entitled "Raman Chemical Imaging of Breast Tissue", a continuation of U.S. application Ser. No. 10/184,580, now U.S. Pat. No. 6,965,793, filed on Jun. 28, 2002 entitled "Method for Raman Chemical Imaging of Endogenous Chemicals to Reveal Tissue Lesion Boundaries in Tissue", and a continuation of U.S. application Ser. No. 10/185,090, now U.S. Pat. No. 6,954,667 entitled "Methods for Raman Chemical Imaging and Characterization of Calcification in Tissue". U.S. application Ser. No. 11/361,256 also claims priority to U.S. Provisional Application No. 60/656,057 filed on Feb. 24, 2005 entitled "Raman Chemical Imaging to Determine Tissue Margins During Surgery", and to U.S. Provisional Application No. 60/301,708 filed on Jun. 28, 2001, entitled "Method for Objective Evaluation of Tissue Using Raman Imaging Spectroscopy". The instant application also claims priority to U.S. Provisional Patent Application No. 61/199,236, entitled "Raman Chemical Imaging of Threat Agents Using Pulsed Laser Excitation and Time-Gated Detection", filed on Nov. 14, 2008. These applications are hereby incorporated by reference in their entireties.

FIELD OF THE DISCLOSURE

This application relates generally to the evaluation of biological tissue and to the use of pulsed laser excitation, time-gated detection, and Raman spectroscopic methods including Raman spectroscopy and Raman chemical imaging for differentiating a margin of neoplastic tissue from a margin of non-neoplastic tissue in a biological sample.

BACKGROUND

The detection of tissue margins to surgically remove tumors is highly subjective. Medical personnel would greatly benefit from methods for the quantitative identification of margins, between neoplastic and non-neoplastic tissue. Such methods hold potential for ensuring sufficient tissue near the tumor is surgically removed thereby preventing the reoccurrence of the tumor. Brain tissue is a particularly important case where ill-defined margins may disrupt important functions of the brain.

Current operative microscope methods are inadequate for the intra-operative differentiation of primary central nervous system neoplastic tissue from non-neoplastic tissue. Digital image guidance techniques are hampered by the problems of structural shift which occurs during resection such that the pre-operative images do not correlate to the operative field. Ultrasonographic methods have limitations associated with tissue swelling or the presence of hemorrhage. Neurosurgical investigators have used various injectable dyes or stains to demark tumor margins to resolve the problems associated with the current methods. These injectable agents demarcate boundaries which are limited to a physical process, the breakdown of the blood-brain barrier, rather than identifying specific neoplastic boundaries.

Various researchers have applied Raman spectroscopy to characterize a wide variety of biological tissue as described in: Hanlon et. al., 2000, Physics in Medicine and Biology, 45: R1-R59; Lakshmi et al., 2002, Radiation Research, 157(2), 175-182; Mizuno et al., 1992, Neuroscience Letters, 141 (1), 47-52; Mizuno et al., 1994, Journal of Raman Spectroscopy, 25, 25-29; Sajid et al., 1997, Journal of Raman Spectroscopy, 28, 165-169; Dong et al., 2003, Biochemistry, 42, 2768-2773; and Mirura et al., Journal of Raman Spectroscopy, 2002, 33, 530-535, each of which is incorporated by reference in its entirety.

In the case of brain tissue, Raman spectroscopy has been performed on the cerebral cortex, white matter of the cerebrum and the thalamus, using near infrared illumination. The intensity ratios of the amide I bands compared to bands representative of CH bonds were used to differentiate between grey and white matters. These intensity ratios were also used to distinguish between normal brain tissue and brain tumor. Other studies have shown changes in the Raman spectra of biological and brain tissue of mice after the mice were subjected to irradiation. Raman spectroscopy has also been used to monitor amyloid $\beta$-plaques deposited in the brains with Alzheimer's disease ("AD"). Using NIR illumination, clear differences between the Raman spectra of AD tissue and non-diseased tissue were observed. Features of the Raman spectrum appear indicative of $\beta$-pleated sheet conformation were observed for amyloid $\beta$-protein in senile plaques. The lipid-to-protein intensity ratios were used to monitor disease-related changes in the tissue composition.

Chemical imaging combines spectroscopy and digital imaging processing to provide image with contrast based on chemical structure that detail morphology, composition and structure. Raman spectroscopy and Raman chemical imaging are non-destructive, non-contact, and require little to no sample preparation. Raman approaches for the evaluation of biological systems including cells and tissue samples have the distinct advantage over reagent-based methodologies because Raman signals can be measured from the molecular constituents of a sample directly. Raman assessment of cell and tissue samples can be applied to a broad group of cells and tissues and even hold potential for assessing the presence and effects of pharmaceutical agents in cellular and tissue systems. The use of Raman techniques also holds potential for demonstrating sensitivity to histological distinctions in tissues.

Historically, instruments have used Continuous Wave (CW) laser sources to excite the sample being analyzed. One challenge in deploying a Raman imaging or spectroscopic system in the setting of living tissues is the amount of fluorescence present in tissues due to endogenous fluorophores. This fluorescence may interfere with the Raman signal the sample is exhibiting. Autofluorescence of the sample often plagues CW Raman. With repeated laser exposure, fluorescence will often decrease through the process of photobleaching. Photobleaching can be time consuming, ranging anywhere from minutes to hours. A second challenge is the effect of background or ambient light on Raman measurements, which make Raman detection in many settings more difficult. There exists a need to rapidly analyze a biological sample while simultaneously reducing the effects of autofluorescence. Specifically, such systems and methods are needed to advance analysis of biological tissue samples, specifically to enable differentiation between tissue margins.

SUMMARY

The present disclosure provides for a system and method for differentiating between tissue margins using pulsed laser excitation and time-gated detection in conjunction with Raman spectroscopy and Raman chemical imaging. Pulsed laser excitation and time-gated detection provides for greatly reduced measurement times and enhanced SNR because much of the fluorescence may be time-gated out of the detection. This is possible because Raman signal is given off about 1 picosecond after laser exposure while fluorescence is not generated until after 1 or 2 nanoseconds of laser exposure.

The present disclosure provides for a system and method that are advantageous over CW laser/non-gated detection for analyzing biological material in an imaging format. One aspect of the present disclosure provides for gated detection of Raman photons while using a whole field of view detector, as in a tunable filter. This allows Raman chemical imaging of samples using a wide field illumination and detection system in a setting where the gating of the detection reduces the background fluorescence of the sample. This will improve signal to background measurements in Raman scattering samples which also exhibit fluorescence under the illumination of the laser used to excite Raman scattering.

The systems and methods provided for herein are significant because they hold potential for allowing an operating surgeon to see aspects of the surgical field which are currently not visible. This includes the chemical makeup of the tissue that is determined by the local physiology and therefore pathology. This can be extremely important when there is a decision about where the end of a histological type (tumor vs. Normal border) exists. These decisions are made on the spot by a surgeon based on the color, and occasionally the feel, of the tissue being assessed. The system and method of the present disclosure holds potential for laying the foundation of techniques that would enable a physician to be able to visualize the chemistry of a tissue under examination.

In addition, the systems and methods described herein hold potential for providing the surgeon with better objective visualization. This is an important step in providing automated surgical systems information which is needed for more autonomous operation. For example, it is contemplated herein that a robotic surgical system could detect when it is about to cut into an important nerve or blood vessel, making it less likely to make such an error and resulting in a more accurate and reliable procedure.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE EMBODIMENTS

Figure 1:
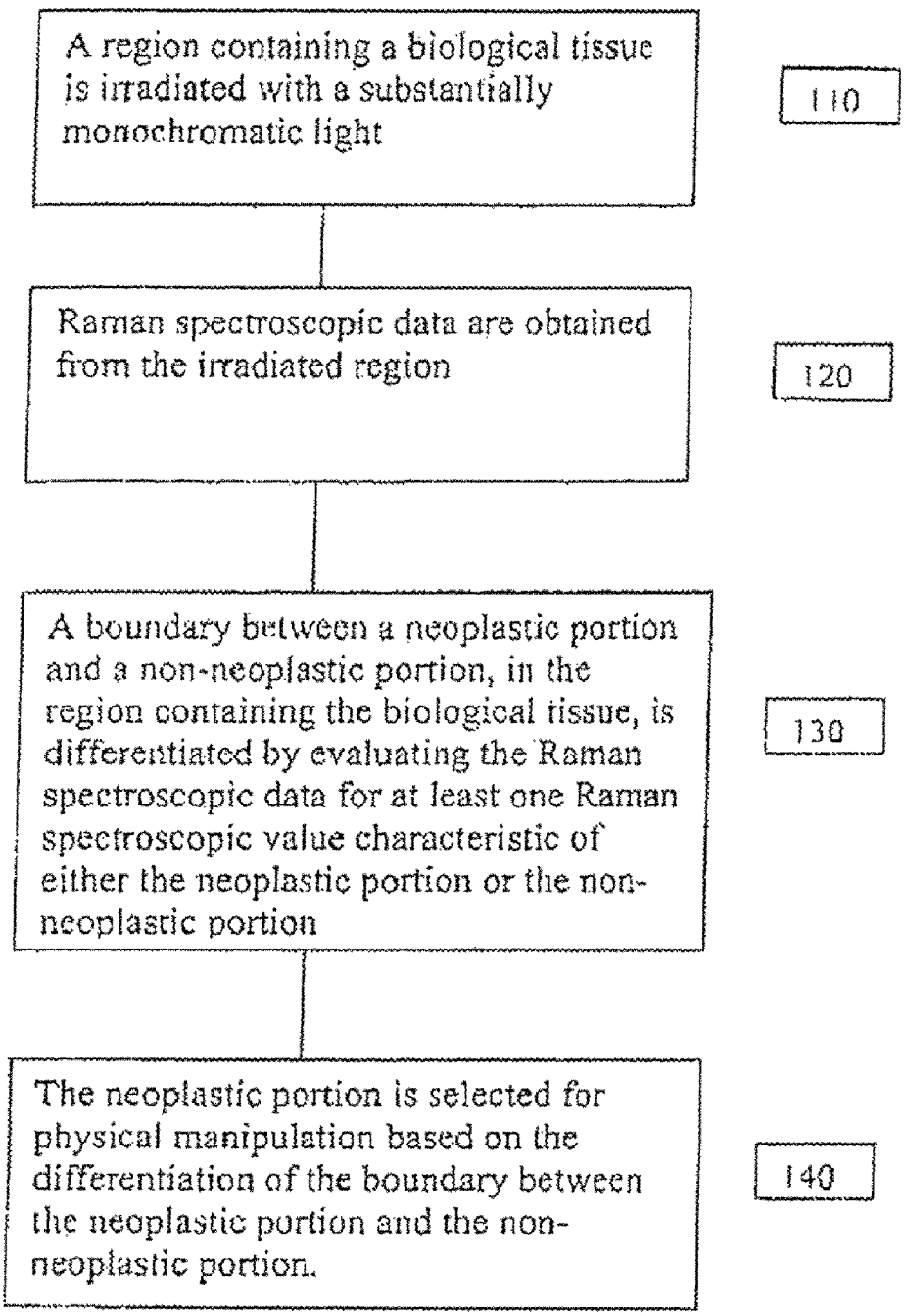
FIG. 1 is a flow chart representing a method of the present disclosure.

Reference will now be made in detail to the embodiments of the present disclosure, examples of which are illustrated in the accompanying drawings. Wherever possible, the same reference numbers will be used throughout the drawings to refer to the same or like parts.

The present disclosure provides for a method to differentiate tissue margins during various medical procedures. Raman spectroscopy will be used to differentiate the margins of neoplastic and non-neoplastic biological tissue. This will be accomplished by detection of molecules indicative of neoplastic and non-neoplastic tissue. In one embodiment, the inventors will use Raman chemical imaging to identify the neoplastic and non-neoplastic tissue. The Raman spectra and Raman images will be molecule-specific and thus more specific than images derived from stains.

Differences, in the Raman spectra of molecules and tissue within biological tissue, in an irradiated region, will be used to differentiate boundaries of neoplastic from non-neoplastic tissue. The ability to differentiate these boundaries results from the presence of endogenous molecules, within the tissue, that are indicative of a boundary between a neoplastic portion and a non-neoplastic portion of biological tissue. The Raman spectral data may be collected using non-imaging Raman microspectroscopy or as spatially resolved independent Raman spectra at various Raman shift values. The spatially resolved Raman spectra may be collected in at least one direction. In a typical Raman chemical imaging experiment, a specimen is illuminated with monochromatic light, and the Raman scattered light is filtered by an imaging spectrometer which passes only a single wavelength range. The Raman scattered light may then be used to form an image of the specimen. A spectrum is generated corresponding to millions of spatial locations at the sample surface by tuning an imaging spectrometer over a range of wavelengths and collecting images intermittently. Changing the selected band pass (wavelength) of the imaging spectrometer to another appropriate wavelength causes a different material to become visible. A series of such images can then uniquely identify constituent materials, and computer analysis of the image is used to produce a composite image highlighting the information desired. Although Raman chemical imaging is predominately a surface technique, depth-related information can also be obtained by using different excitation wavelengths or by capturing chemical images at incremental planes of focus. Contrast is generated in the images based on the relative amounts of Raman scatter or other optical phenomena such as luminescence that is generated by the different species located throughout the sample. Since a spectrum is generated for each pixel location, chemometric analysis tools such as correlation analysis, Principle Component Analysis (PCA) and factor rotation, including Multivariate Curve Resolution (MCR) can be applied to the image data to extract pertinent information otherwise missed by ordinary univariate measures. Several Raman chemical imaging ("RCI") technologies have evolved including point scanning RCI, line imaging RCI, liquid crystal tunable filters RCI and fiber array spectral translator ("FAST") technology.

Raman spectroscopy may be coupled with other spectroscopic and imaging techniques to aid in the differentiation of neoplastic tissue from non-neoplastic tissue. These spectroscopic and imaging techniques include transmission or reflectance modes; fluorescence; ultraviolet; infrared; near infrared; mid infrared; far infrared; visible; photoluminescence; chemiluminescence; and electroluminescence imaging. The Raman spectrometer may also operate in conjunction with polarized light microscopy and/or differential interference contrast imaging.

In one embodiment, the entire field of view to be investigated is illuminated simultaneously using an approach called wide-field illumination. This illumination strategy yields Raman scattered light from each point within the field of view simultaneously. Measurement of this Raman scattered light from each point within the field can be accomplished by using a set of collection optics to collect the light emanating from the field of view. The collected light is filtered, using optical components, to provide Raman scattered light preferentially to a detector. Optical components used to filter the collected light include combinations of band pass and band rejection filters. For example a band rejection filter is used to reject the substantially monochromatic illumination light. Simple band pass filters can be used to preferentially select the Raman scattered light for detection, however, a preferred approach is to use a tunable filter to select light at a series of Raman shifts from the wavelength of illumination. Raman spectroscopic data from the field of view is frequently structured as what is known in the art as an image hypercube which is a series of 2 dimensional images at different points in spectral space. Each pixel in such a hypercube represents a spectrum of the position in the measured field of view over the spectral variable chosen for the measurement.

With reference to FIG. 1, a region containing a biological tissue is irradiated, with a substantially monochromatic light. In step 120, Raman spectroscopic data is obtained from the irradiated region. In step 130, a boundary between a neoplastic portion and a non-neoplastic portion, in the region containing the biological tissue, is differentiated by evaluating the Raman spectroscopic data for at least one Raman spectroscopic value characteristic of either the neoplastic portion or the non-neoplastic portion. In step 140, the neoplastic portion is selected for physical manipulation based on the differentiation of the boundary between the neoplastic portion and the non-neoplastic portion. In one embodiment, the steps of irradiating, obtaining, differentiating and selecting takes place in vivo on a region of biological tissue of a patient. The Raman spectroscopic value includes a Raman shift for one of the following the neoplastic portion and the non-neoplastic portion.

In one embodiment, the step of differentiating a boundary between neoplastic portion and non-neoplastic portion in the irradiated region includes correlating the Raman spectral data with a visible image of the same region. A means for correlating the visible image and the Raman spectral data includes fusing the images using software. While Raman detector and visible cameras often generate images having differing contrast, the sample fields of view can be matched through a combination of optical and software manipulations. As a result, the Raman spectral data and visible images can be compared and even fused through the use of overlay techniques and correlation techniques to provide the user a near-real time view of both detector outputs on the same computer display. The comparative and integrated views of the sample can significantly enhance the understanding of sample morphology and architecture. By comparing the visible images and Raman spectral data, additional useful information can be acquired about the chemical composition, structure and concentration of species in samples.

In one embodiment, the method further comprises physically manipulating one of the neoplastic portion and the non-neoplastic portion. The physically manipulating the neoplastic portion may comprise excising the neoplastic portion from the region containing said biological tissue.

In another embodiment of the present disclosure, the method may further comprise differentiating, selecting, and excising the selected neoplastic portion are performed iteratively. The steps of differentiating, selecting and excising the selected neoplastic portion may be performed iteratively and may also take place in vivo on a region of biological tissue of a patient. In another embodiment, the present invention may further comprise rinsing the region containing biological tissue between the steps of selecting and excising. The step of rinsing the region may also take place in vivo on a region of biological tissue of a patient.

Physical manipulation of the neoplastic tissue may comprise a variety of procedures including: applying radioactive material to the neoplastic portion; applying a cryogenic agent to the neoplastic portion; applying heat to the neoplastic portion such as thermal ablation; extirpation of the tissue; applying electrical current to the neoplastic portion; applying a chemotherapy drug to the neoplastic portion; applying a gene therapy treatment to the neoplastic portion; radiation of the tissue; implantation of the tissue with therapeutic delivery systems; irradiating the neoplastic portion with radiation having a wavelength corresponding to a photoactivatable cytotoxic agent; any other methods which would lead to the elimination of the abnormal area.

Means useful to select the neoplastic portion for physical manipulation include: a visual display; a head mounted display; a system for projecting the information directly onto the operative field of view; and a system for projecting the information directly on the retinal of the operator. Means or tools useful for the physical manipulation of the neoplastic and non-neoplastic tissue include: a cryotherapy probe; a radiation treatment applicator; an electronic surgical cutting tool; a laser used to ablate tissue; and a thermal applicator to apply localized heat to the sample.

The physical manipulation of the neoplastic portion may also take place in a variety of settings in which a manipulation of abnormal tissue may occur. The settings may include but are not solely limited to one of the following: an operating room; a procedure room; a radiology or radiation oncology suite; or a medical practitioner's office.

Figure 2:
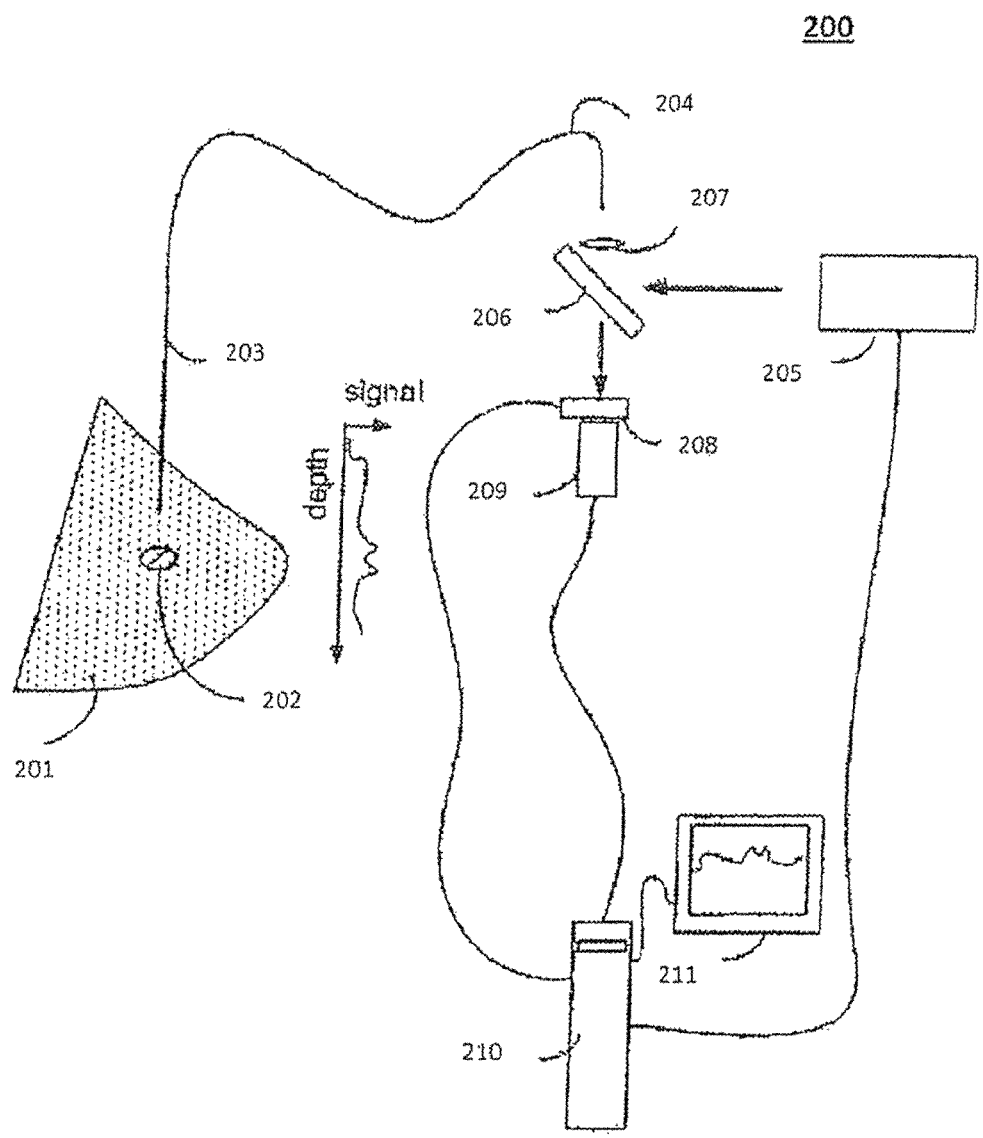
FIG. 2 is a schematic representation of a system of the present invention.

An in vivo embodiment of the invention, for examining biological tissue 201 to differentiate the boundary between neoplastic 202 and non-neoplastic tissue 201 is illustrated in FIG. 2. An endoscope or other instrument 203 is used to introduce light carried by an optical fiber 204 from a monochromatic light source 205. A dichroic mirror 206 and lens 207 are shown schematically for introducing the light into the fiber 204. Raman light from the biological tissue is carried from the tissue back through the lens 207 and mirror 206, through a filter 208 to a detector 209. The signal from the detector 209 is analyzed by a computer system 210 and displayed on a monitor 211.

In one embodiment of system 200, the Filter 208 is an Evan's split element liquid crystal tunable filter, which is controlled by computer 210. However, it is contemplated by the disclosure that other tunable filters may be used, including but not limited to, Liquid Crystal Tunable Filter (LCTF), Acousto-Optic Tunable Filter (AOTF), Multi Conjugate Filter (MCF).

In one embodiment, the endoscope 203 is an imaging endoscope or fiberscope, where light is conducted from the tissue to the detector 209 in a coherent manner through a large plurality of optical fibers. A series of two dimensional images is preferably taken as a function of depth into the tissue and of the Raman shifted wavelength.

A typical operating scenario for this approach is to use an image recording device such as a CCD camera or CMOS based digital imaging system to record an image of the light which emanates from the operative field of view. The recording of the light must be performed in a way that allows spectral resolution of Raman scattering features characteristic of the materials, in this case tissues, in the field of view. A typical approach to record such an image is to use a CCD or CMOS detector to detect light which has passed through a narrowband tunable filter. Several types of tunable filters can be used to filter the light prior to detection including but not limited to Liquid Crystal Tunable Filter (LCTF), Acousto-Optic Tunable Filter (AOTF), Multi Conjugate Filter (MCF). Images are recorded at distinct set points of the tunable filter and treated as a stack of images in spectral space, known in the art as a hyperspectral image. There are alternative approaches to generate a hyperspectral image including Computed Tomography Imaging Spectroscopy (CTIS) which can be employed if the alternative approaches have the spectral resolution to resolve Raman features (typically less than 20 $cm^{-1}$).

In order to generate discernable Raman scatter the field of view which is the focus of study must be illuminated by a substantially monochromatic source such as a laser. In one embodiment, in addition to the hyperspectral image of the field of view with high spectral resolution, a low spectral resolution image such as is obtained under the illumination of broadband light can also be acquired. This can be obtained for instance with "white light" illumination and a standard color digital imaging camera.

The data from the hyperspectral image is processed to account for measurement artifacts including wavelength dependent transmission and detection variations caused by the optics and detectors. This is performed in standard fashion by making a measurement of the optical characteristic of the measurement system using known standards and determining the optical performance of the whole system.

After instrument response correction of the raw data, the spectroscopic features within the pixels which comprise the image are used to create an image which can guide the operator in terms of the location of neoplastic or non-neoplastic tissue. Creation of this guide image involves application of one or more of different data processing technique collectively known as multivariate approaches. These include techniques such as principal component analysis (PCA), Cosine Correlation Analysis (CCA), Euclidian Distance Analysis (EDA), multivariate curve resolution (MCR), Band T. Entropy Method (BTEM) Mahalanobis Distance (MD), Adaptive Subspace Detector (ASD) to name exemplary modes. Substantially any method which takes advantage of the spectral information in the hyperspectral image could be employed.

In some cases multivariate methods are employed on a dataset and can be used without the dependence on an external reference sample. In other cases multivariate methods can be used to interpret data based on some reference information. In a typical example of this approach, the distinctive spectral differences between neoplastic and normal tissue, for example brain tissue, can be used as a basis for applying multivariate techniques to classify each pixel in an image as normal or neoplastic tissue.

Once the raw hyperspectral data is instrument corrected and interpreted, using multivariate techniques, it can be fused with the normal "white light" image of the field of view. This enables the operator to see an image of the operative field of view with information about a neoplastic state mapped, for example, in a particular color.

Figures 3A, 3B:
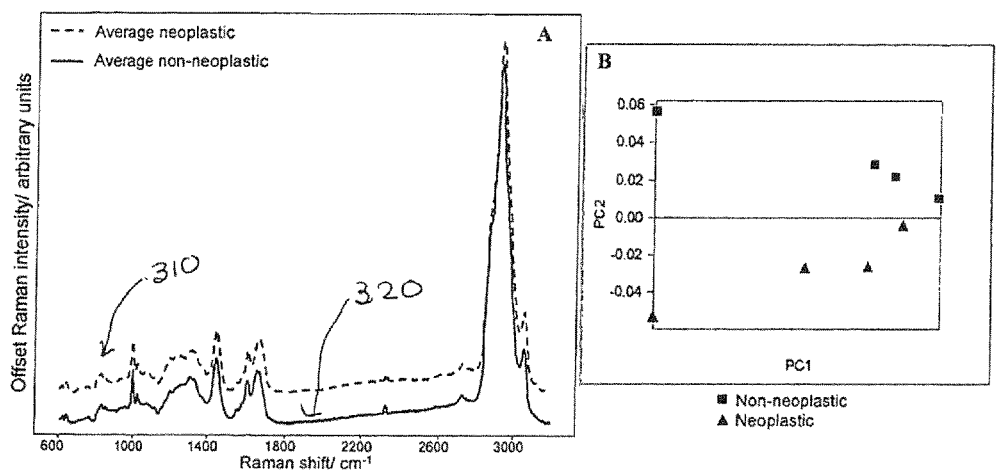
FIGS. 3A and 3B illustrate an average Raman dispersive spectrum of non-neoplastic and neoplastic tissue and the principal component analysis scores plot demonstrating the ability to distinguish between non-neoplastic and neoplastic tissue.

FIG. 3A compares the Raman dispersive spectra of neoplastic and areas of non-neoplastic brain tissue. Each spectrum is an average of 5 replicates. Brain tissue samples were removed during routine surgery and prepared using standard sample preparation techniques, including paraffin embedding and microtome sectioning. Sections were placed on aluminum-coated microscope slides and the paraffin removed using standard methods. Spectrum 310 corresponds to neoplastic tissue and spectrum 320 corresponds to non-neoplastic tissue. FIG. 3B is the Principal Component analysis score plot of this data, demonstrating that the two sets of data are distinguishable.

Figure 4:
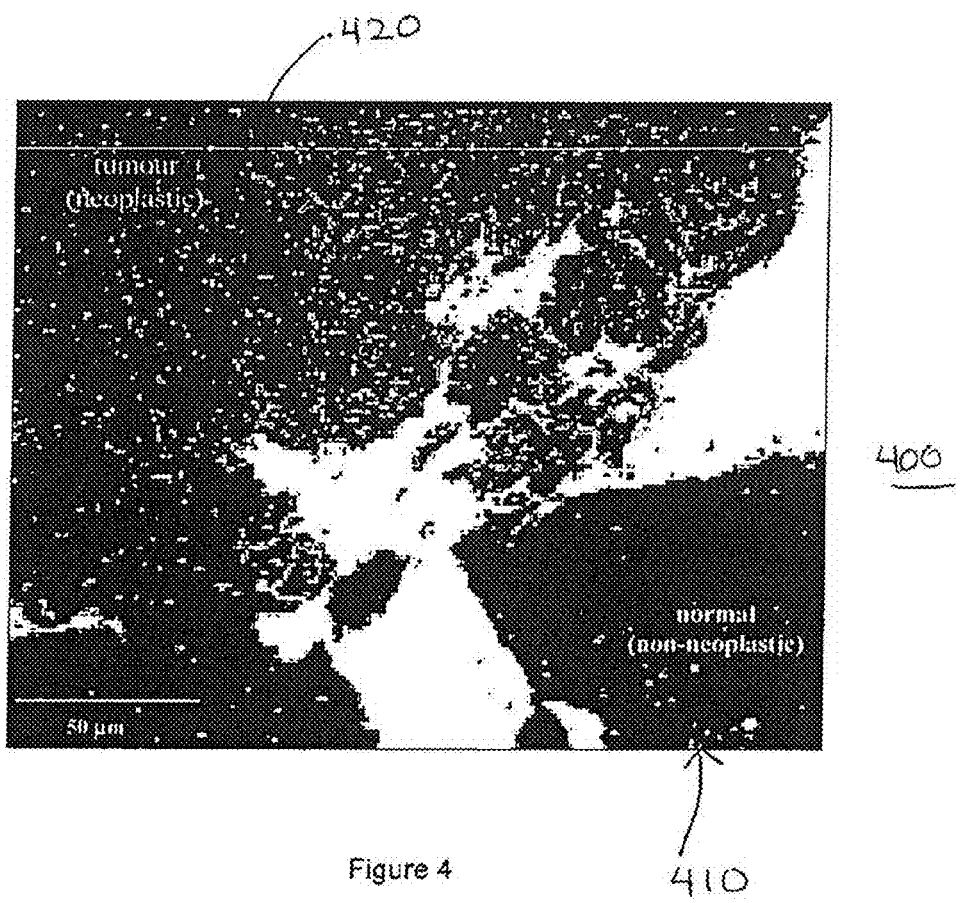
FIG. 4 illustrates a microscopic view of non-neoplastic and neoplastic brain tissue.

FIG. 4 shows a microscopic view 400 of brain tissue which was prepared as described for FIGS. 3A and 3B. In this section, there are clear areas of neoplastic tissue 420 and areas of non-neoplastic tissue 410 as indicated by a pathologist. Although this tissue in particular was not imaged, the data illustrated in FIGS. 3A and 3B indicate that neoplastic and areas of non-neoplastic tissue have different Raman signals, and would be distinguishable in an image such as FIG. 4.

Figure 5:
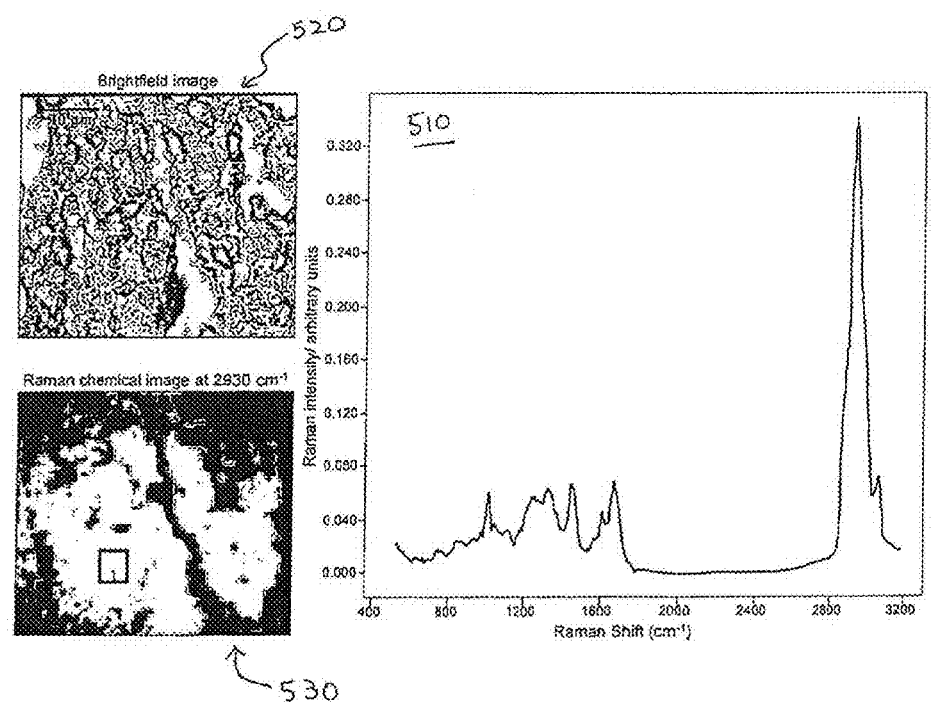
FIG. 5 illustrates a Raman chemical image of neoplastic brain tissue.

FIG. 5 illustrates a Raman chemical image of neoplastic brain tissue which was prepared as described for FIGS. 3A and 3B. Image 520 corresponds to the bright field image of the irradiated brain tissue and image 530 corresponds to the Raman chemical image at 2930 cm.sup.−1. The Raman chemical image is derived from the distinct spectral Raman data 510 for the neoplastic brain tissue.

The above example can be carried out using a system comprising: a substantially monochromatic light source coupled to a means for light delivery which directs the light to the region containing a biological tissue: a Raman spectrometer system with or without imaging capability optically coupled to the region of interest and capable of acquiring measurements of Raman scattered light from the region: a software module for differentiating a boundary between neoplastic portion and non-neoplastic portion in the region based on evaluation of measurements of Raman spectroscopic measurements: a module, such as a visual display which depicts the region on a screen, for allowing selection of the distinctive portions for manipulation. Such a system can further comprise a broadband illumination and image capture channel to facilitate display of the Raman based information in the context of the visual appearance of the region of interest. Operative tools consistent with a desired manipulation may be integrated into the system.

In one embodiment, the system would comprise 532 nm laser coupled to a laser delivery fiber with a short pass scrub filter at the distal end to remove any contribution of the fiber to the illumination light directing substantially monochromatic light to a region of tissue. Integrated into this delivery fiber is a fiber based light collection system which collects light emanating from the field of view while blocking the illumination light from entering the collecting fiber. The output of the collection fiber is coupled to a Liquid Crystal Tunable Filter. The output of the LCTF is coupled to a cooled CCD camera for data acquisition. A software module controls data acquisition and processing rendering an image of the region of tissue which carries information about the spatial distribution of neoplastic and non-neoplastic tissue within the region. A LCD display system displays the rendered image in a fashion that the operator is allowed to select neoplastic tissue for manipulation using operative manipulative tools such as a scalpel.

Figure 6:
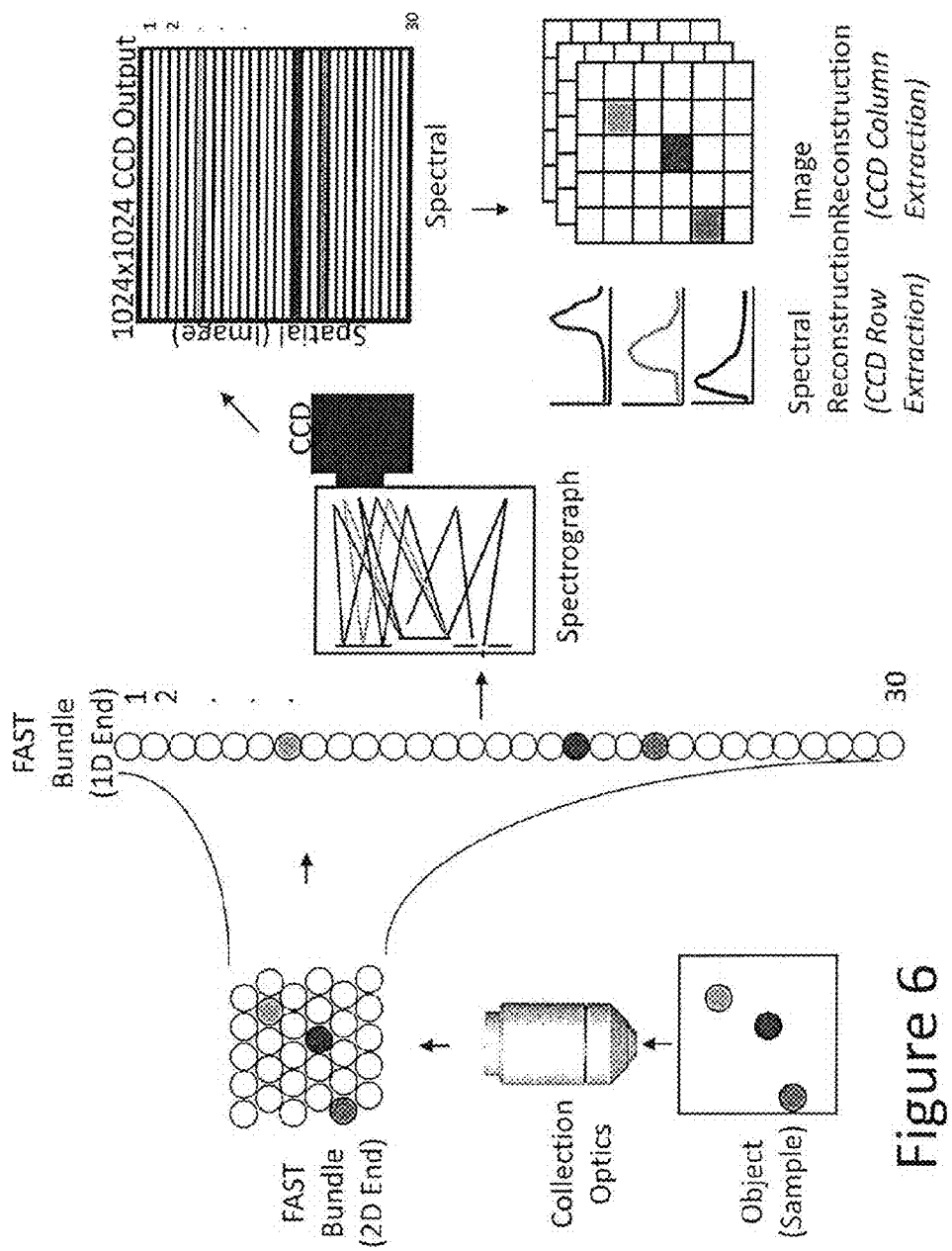
FIG. 6 illustrates of the Fiber Array Spectral Translator (FAST) concept.

FIG. 6 is representative of the Fiber Array Spectral Translator (FAST) concept. With FAST, light from the sample is focused onto a 2D bundle of optical fibers that is drawn to a linear array of fibers at the opposite end. The 1D end is positioned at the entrance slit of a dispersive spectrometer. A set of spatially resolved spectra and spectrally resolved images are reconstructed from the dispersed light detected from individual fibers on a single CCD image.

A Fiber Array Spectral Translator ("FAST") system when used in conjunction with a photon detector allows massively parallel acquisition of full-spectral images. A FAST system can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST to the detector rows of the photon detector.

Figure 7:
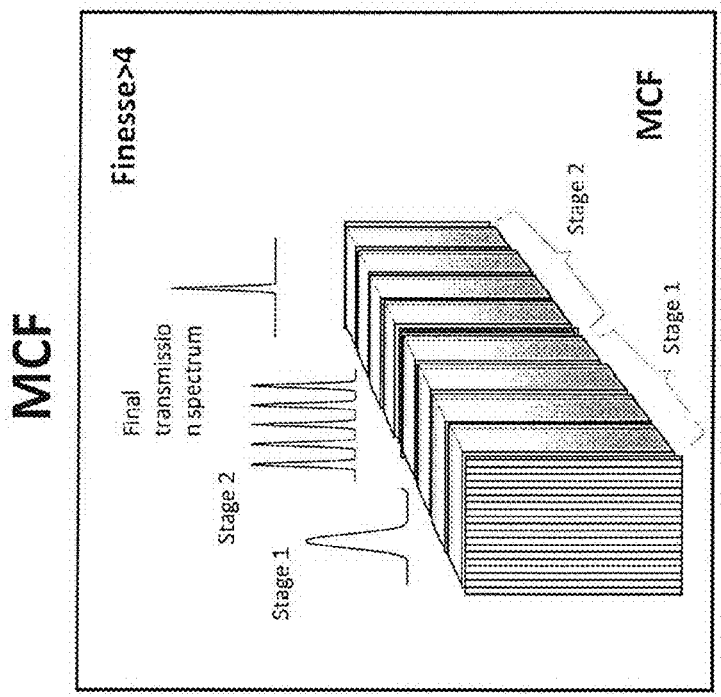
FIG. 7 illustrates an overview of the Multi-Conjugate Filter (MCF) concept.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the photon detector. Given the advantageous ability of a FAST system to acquire hundreds to thousands of full spectral range, spatially-resolved spectra, such as Raman spectra, substantially simultaneously, a FAST system may be used in a variety of situations to help resolve difficult spectrographic problems FIG. 7 is an overview of the Multi-Conjugate filter (MCF). MCF is a no moving parts, electro-optical device that may be tuned to discrete energies (i.e. wavelengths) of light. Light traversing the filter onto a CCD or focal plane array detector enables wavelength-specific images to be captured. The MCF is a filter that has much improved thermal stability and throughput, especially for green and blue wavelength regions compared to ordinary Liquid Crystal Tunable Filters (LCTFs). Another attribute of the MCF includes high finesse stages that substantially reduce the number of polarizers.

The present disclosure also provides for a system for analyzing a tissue sample using pulsed laser excitation and time-gated detection for Raman chemical imaging of biological samples. This system integrates the use of pulse laser excitation and time-gated detection with the use of a liquid crystal tunable filter. The pulsed laser and time-gated detector provide the timing and rejection necessary to reduce the effects of ambient light and fluorescence, while the LCTF provides the spectral discrimination necessary to perform Raman imaging. The apparatus enables novel application of detection of tissue margins in biological samples in the form of Raman chemical images. In one embodiment, a laser light source is modulated either in the form of a narrow pulse or at a single high frequency. One skilled in the art will provide appropriate light conditioning prior to the impingement of light on the sample when necessary.

In one embodiment, the system may include focusing optics such as an objective or "scrub filters" to remove Raman radiation scattered from the propagation medium (the optical fiber for example). In another embodiment, light scattered from the sample is collected using a collecting optical element. In one embodiment, this can be a set of lenses such as the objective of a microscope, the input lens of and mirrors of a telescope, or the input of a fiber optic bundle. Optical elements can be selected in to reject the illumination light from the source and placed in an appropriate position in the collection optical system. After the light is collected it can be transmitted to the input face of a liquid crystal based tunable filter. The light can also be transmitted to the input face of a multi-conjugate tunable filter (MCF). The tunable filter is used to select only a specific wavelength of light for detection. Light which passes the tunable filter is directed to a camera for detection. A Raman image is made by acquiring an image from the camera at a series of selected wavelength settings of the tunable filter. In one embodiment, the system also comprise a suitable computer control system for controlling the components of the system and recording and storing data collected by the system.

In one embodiment, the present disclosure provides for a system that further comprises an optical element capable of gating (changing transmission states from open to closed) very rapidly. In one embodiment, this optical element is located in the light collected optics. In another embodiment, the optical element is located in the collected light transmission optics, between a sample and a detector camera. One such technology that is contemplated by the present disclosure is a microchannel plate image intensifier. In one embodiment, a microchannel plate image intensifier is integrated with the camera as a single unit.

In another embodiment of the present disclosure, the system provides for amplification of signals and temporal gating. The amplification comes from the acceleration of photoelectrons through channels which are in a large electric field (to provide acceleration), but arranged misaligned to the direction of the field so that electrons are accelerated into the walls of the channel. This causes more electrons to be released thus, amplifying the number of electrons and therefore the signal. The initial signal transduction is through a photoconverting layer which emits an electron when a photon hits the layer. This layer is located between the incoming light and the microchannel plate and the voltage of appropriate size and bias can be applied across the gap between the layer and the entrance to the microchannel plate to either direct the photoelectrons to enter the microchannel plate or not enter the microchannel plate. By changing this voltage, the system is effectively gated.

The gating system described herein will generate electrons for many different wavelengths of light, but the electrons will not carry information about the energy or wavelength of the incident photons. Thus, in one embodiment the system, a detector element would be located after a tunable filter but before a detector camera.

The systems and methods of the present disclosure can be operated in at least two modes: time-domain mode and frequency-domain mode. In time-domain mode, when using a pulsed laser, the gate for the microchannel plate may be synchronized to the laser in such a way that the gate is only opened for a brief time after the pulse of light has hit the sample and the light collected thereafter from the sample is traveling through the optical system, and the lifetime of the fluorescence which is to be rejected. The closer the gate is to the initial photons which are collected from the sample after the interaction of the illuminating pulse with the sample, the more fluorescence can be rejected.

In frequency-domain mode, when using an intensity modulated laser, the gate for the microchannel plate can be operated at the same frequency as the laser modulation and adjusted in phase. This mode is usually referred to as homodyning. Through proper adjustment of the phase of the source and detector frequency of modulation and application of appropriate mathematical models, and accounting for fluorescence and ambient light can be achieved.

In an alternative embodiment of the frequency-domain mode, the apparatus is configured to operate the laser and microchannel plate detector at high, but slightly different frequencies. This approach is commonly called heterodyning. Through appropriate choice of these frequencies and appropriate operation of the detector camera, measurement of the phase, AC and DC components at one or more base frequencies can allow independent estimation, and in some cases determination of the Raman signal and fluorescence signal, allowing for the construction of a Raman and or fluorescence image.

In the frequency-domain embodiments, a tunable filter is positioned before the modulated component of the detector system (including gate and camera) in the optical path so that the wavelength selection is performed with the tunable filter and detection is performed with the combination of gate and camera.

Figure 8:
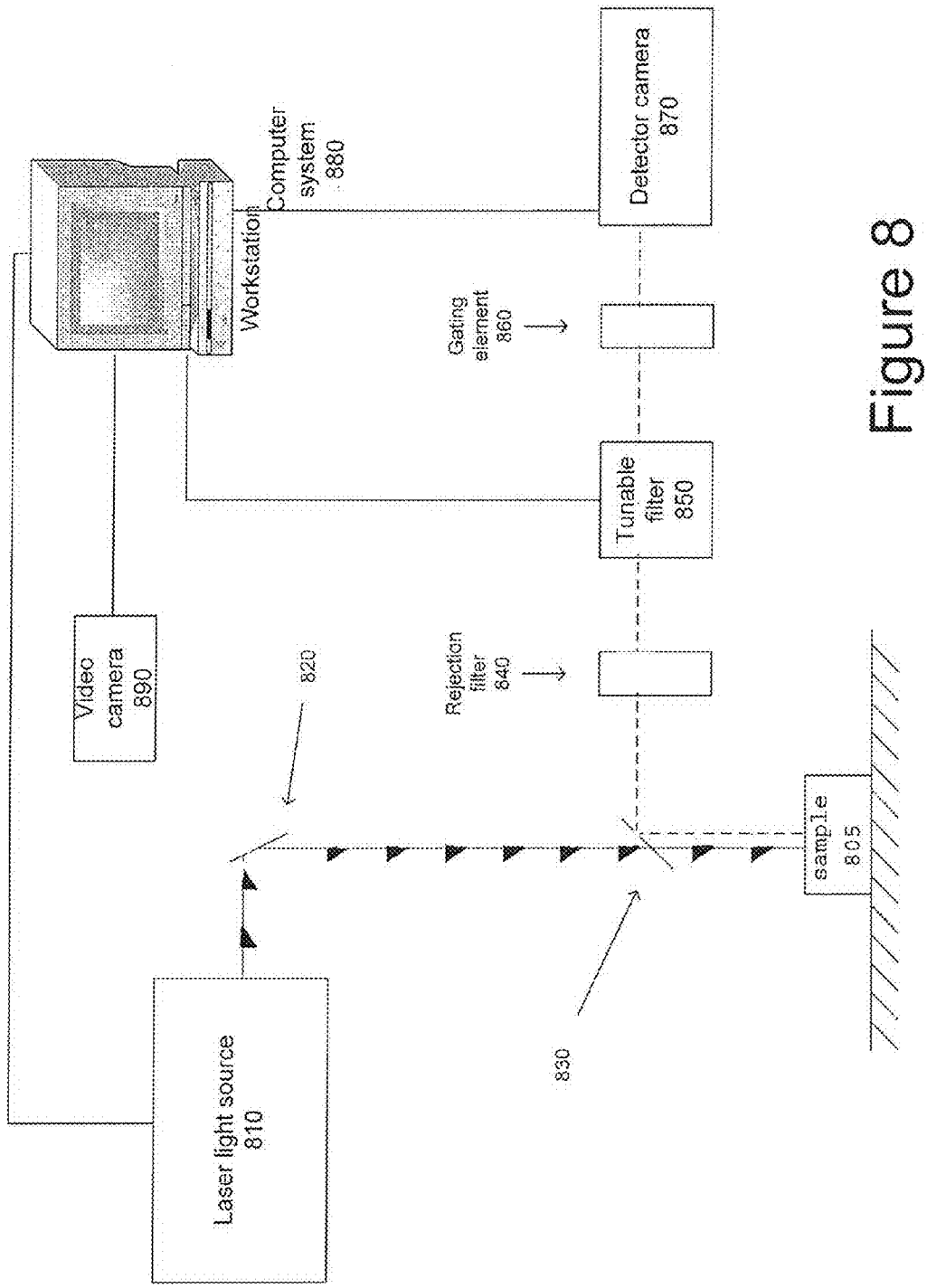
FIG. 8 is a representation of a system of the present disclosure.

One embodiment of a system of the present disclosure is illustrated in FIG. 8. The system 800 comprises a laser light source 810 for irradiating a region of a sample 805 containing a biological tissue with illuminating photons to thereby produce Raman scattered photons. The laser light source may comprise a pulsed laser light source or an intensity modulated laser light source. The light produced by the source must be delivered to the region of the sample. A first optics 820 directs illuminating photons to said region of the sample 805. In another embodiment, the light can be delivered directly through the use of mirrors and lenses. The light can also be propagated through a light guide such as a rigid telescope or laparoscope or through a flexible filter.

A second optics 830 collects said photons Raman scattered from said region of said sample 805. An illumination light rejection filter 840 is configured to block light of a first wavelength and allow light of a second wavelength to pass through said illumination light rejection filter wherein said light of a second wavelength comprises said Raman scattered photons. A tunable filter 850 receives said Raman scattered photons and passes ones of said Raman scattered photons having a wavelength in a predetermined wavelength band. In one embodiment, the tunable filter comprises a liquid crystal tunable filter. In another embodiment, element 850 may comprise a filter selected from the group consisting of: selected from the group consisting of a Fabry Perot angle tuned filter, an acousto-optic tunable filter, a liquid crystal tunable filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, and a liquid crystal Fabry Perot tunable filter. A gating system 860 is configured to open at a specified time, allowing said Raman scattered photons to pass through to a detector camera, thereby generating a Raman spectroscopic image of said region of said sample. In another embodiment of the present disclosure, the gating system 860 may comprise a microchannel plate image intensifier. Other embodiments provided for by the present disclosure may incorporate the use of at least one of pockels cell, Kerr shutter, vanadium dioxide thin film shutter, polarization-discriminating Mach-Zehnder optical switch, and suitably designed photonic crystal based shutters. The present disclosure also contemplates the use of a laser as a gating element. In one embodiment, this laser is the laser light source that illuminates a region of a sample. In another embodiment, this laser can be another laser in addition to the laser light source that illuminates a region of a sample. The system may also comprise the use of spatial propagation (i.e. Spatially Offset Raman Spectroscopy, "SORS") as a type of switching mechanism.

In yet another embodiment, an optical component capable of acting as a gate, or intensity modulator which did not affect the wavelength of transmitted light and had appropriate temporal characteristics could be used in front of the tunable filter as an alternative to placing the gating system after the tunable filter.

The system may also comprise a computer system 880. The computer system can be configured to perform a variety of functions, including but not limited to, controlling the other elements of the system 800, collecting data, and storing the data collected by the system.

In one embodiment, the system further comprises a video camera, which may be a white light video camera. The video camera may be configured to perform a variety of functions, including but not limited to, targeting a region of interest of the sample. The video camera can also be configured to provide for simultaneous imaging in such a way that the Raman information obtained from the gated Raman imaging system could be overlaid with, or fused with the digital image of the sample in real time or off line.

Figure 9:
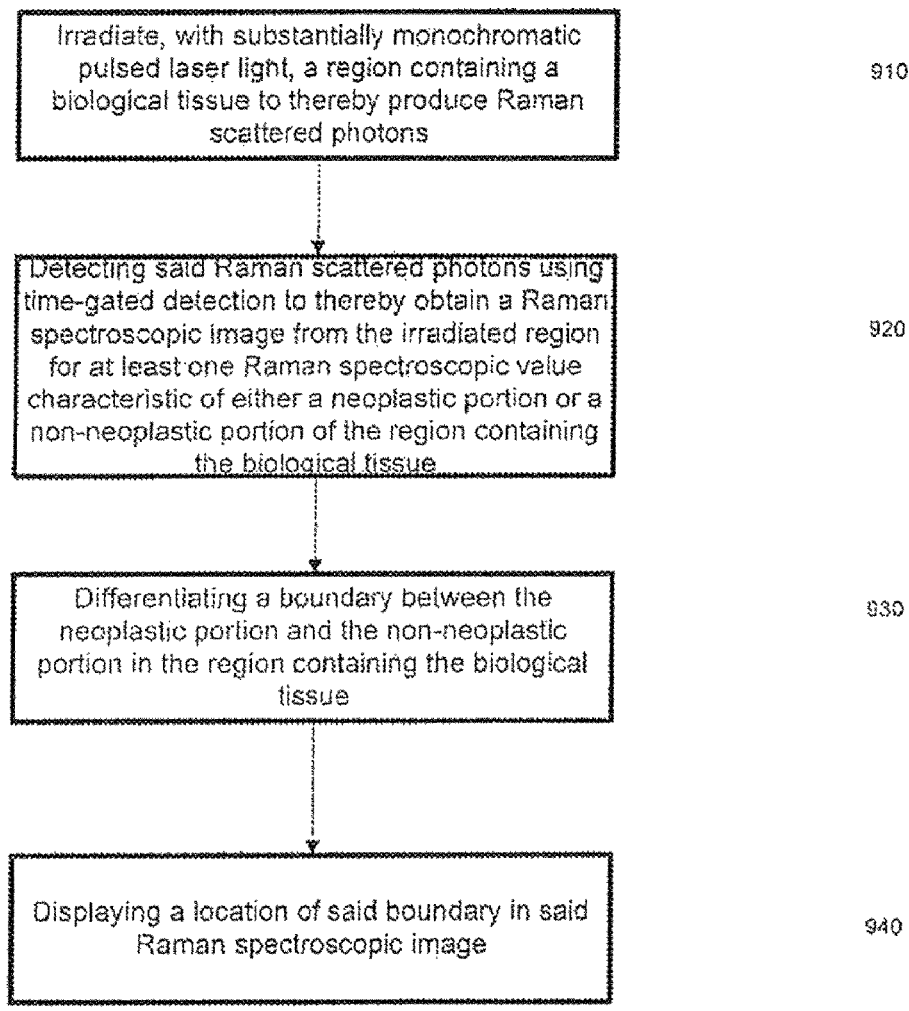
FIG. 9 is illustrative of a method of the present disclosure.

The present disclosure also provides for a method, as is illustrated in FIG. 9. The method 900 comprises irradiating a region containing a biological tissue in step 910 with substantially monochromatic pulsed laser light to thereby produce Raman scattered photons. The biological tissue may comprise, but is not limited to, neurological tissue. The Raman scattered photons are detected in step 920 using time-gated detection to thereby obtain a Raman spectroscopic image from the irradiated region for at least one Raman spectroscopic value characteristic of either a neoplastic portion or a non-neoplastic portion of the region containing the biological tissue. In one embodiment, the Raman spectroscopic image comprises spectral information recorded at each pixel in the image. In one embodiment, said at least one spectroscopic value includes a Raman shift for at least one of: the neoplastic portion and the non-neoplastic portion. In step 930 a boundary between the neoplastic portion and the non-neoplastic portion is differentiated. In one embodiment, said differentiation comprises analyzing said spectral information recorded at each pixel of said Raman spectroscopic image. The location of this boundary in said Raman spectroscopic image is displayed in step 940.

In one embodiment of the method 900, said differentiating comprises analyzing said spectral information recorded at each pixel of said Raman spectroscopic image using a method selected from the group consisting of: principle component analysis, cosine correlation analysis, Euclidean distance analysis, multivariate curve resolution, band t. entropy method, Mahalanobis distance, adaptive subspace detector, and combinations thereof. Said differentiating may also include correlating the Raman spectral image with a visible image of the region.

In another embodiment of the method 900, said boundary location is determined by analyzing said spectral information recorded at each pixel of said Raman spectroscopic image using a method selected from the group consisting of: principle component analysis, cosine correlation analysis, Euclidean distance analysis, multivariate curve resolution, band t. entropy method, Mahalanobis distance, adaptive subspace detector, and combinations thereof.

In one embodiment, the method illustrated in FIG. 9 further comprises selecting at least one of the neoplastic portion or the non-neoplastic portion for physical manipulation. This selecting is based on the displayed boundary location between the neoplastic and non-neoplastic portions. The method may also comprise physically manipulating one or both of the portions. This physical manipulation may be performed in vivo on the region of biological tissue of the patient. The physical manipulation may also comprise excising the neoplastic portion from the region containing the biological tissue.

In one embodiment, the neoplastic portion is physically manipulated by performing at least one of: applying radioactive material to the neoplastic portion, applying heat to the neoplastic portion, applying electrical current to the neoplastic portion, applying a chemotherapy drug to the neoplastic portion, applying a gene therapy treatment to the neoplastic portion, and irradiating the neoplastic portion with radiation having a wavelength corresponding to a photoactivatable cytoxic agent.

Physical manipulation of a portion of the tissue under investigation may take place in, but is not limited to, one of the following settings: a neurological operating room, a neurological procedure room, a radiology suite, and a medical practitioner's office.

In one embodiment, the steps of differentiating, selecting, and excising the selected neoplastic portion are performed iteratively. The steps may also be performed iteratively and in vivo on the region of biological tissue of the patient. The method may also further comprise the step of rinsing the region containing biological tissue between the steps of selecting and excising.

Figure 10:
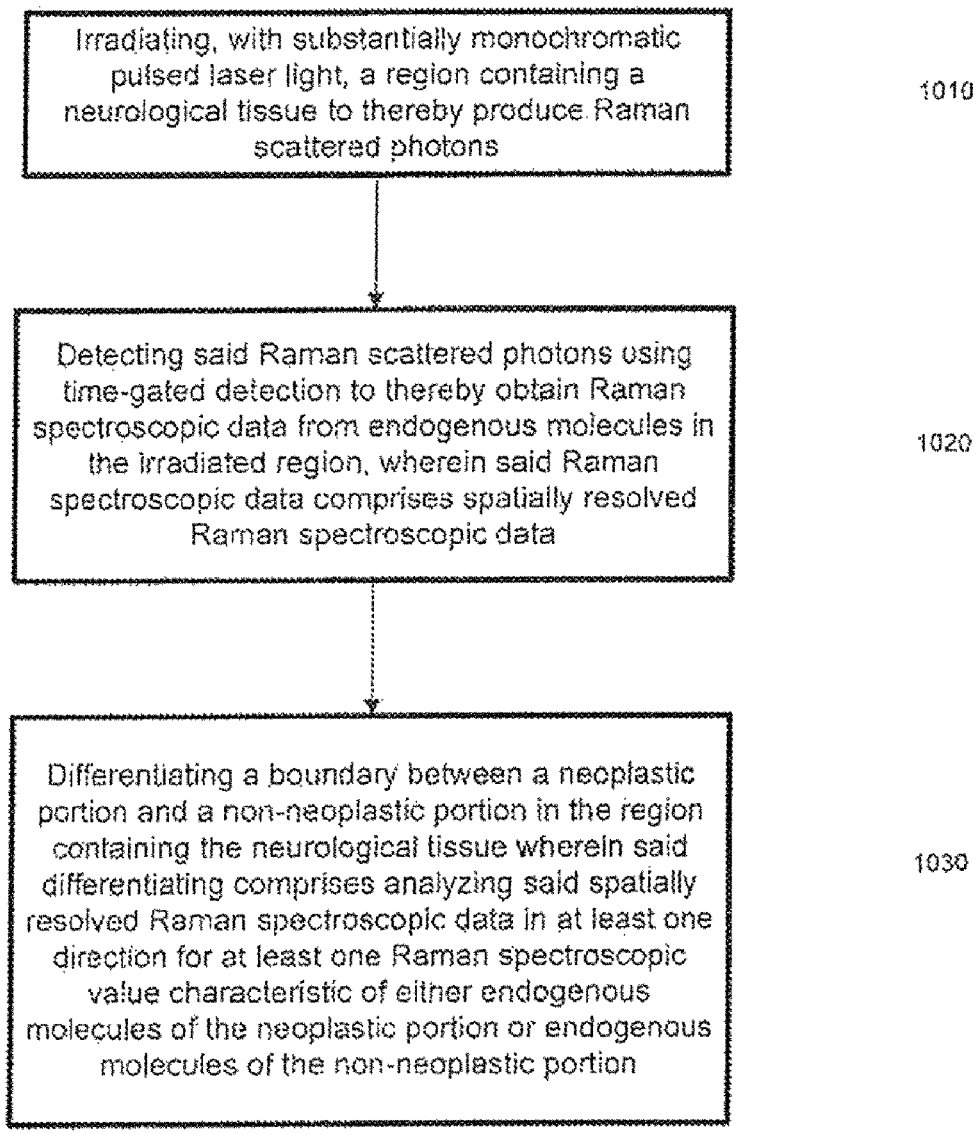
FIG. 10 is illustrative of a method of the present disclosure.

Another embodiment of the present disclosure is illustrated in FIG. 10. The method, 1000, provides for irradiating a region containing a neurological tissue in step 1010 with substantially monochromatic pulsed laser light to thereby produce Raman scattered photons. The Raman scattered photons are detected in step 1020 using time-gated detection to thereby obtain Raman spectroscopic data from endogenous molecules in the irradiated region, wherein said Raman spectroscopic data comprises spatially resolved Raman spectroscopic data. In step 1030 a boundary is differentiated between a neoplastic portion and a non-neoplastic portion in the region containing the neurological tissue wherein said differentiating comprises analyzing said spatially resolved Raman spectroscopic data in at least one direction for at least one Raman spectroscopic value characteristic of either endogenous molecules of the neoplastic portion or endogenous molecules of the non-neoplastic portion.

In one embodiment, method 1000 may further comprise selecting at least one of the neoplastic portion and the non-neoplastic portion wherein said selecting is based on the differentiation of the boundary between the neoplastic portion and the non-neoplastic portion. In another embodiment, said analyzing may comprise using a method selected from the group consisting of: principle component analysis, cosine correlation analysis, Euclidean distance analysis, multivariate curve resolution, band t. entropy method, Mahalanobis distance, adaptive subspace detector, and combinations thereof. The method may also comprise physically manipulating at least one of the neoplastic portion or the non-neoplastic portion. The physical manipulation may be performed in vivo on the region of neurological tissue of a patient.

Said differentiating of method 1000 may further comprise correlating the Raman spectral data with a visible image of the region. In one embodiment, the method may further comprise obtaining a Raman spectroscopic image from the irradiated region for at least one Raman spectroscopic value characteristic of at least one of: the neoplastic portion containing the neurological tissue and the non-neoplastic portion containing the neurological tissue.

The present disclosure may be embodied in other specific forms without departing from the spirit or essential attributes of the disclosure. Accordingly, reference should be made to the appended claims, rather than the foregoing specification, as indicated the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method comprising:
   irradiating, with substantially monochromatic pulsed laser light, a region containing a biological tissue to thereby produce Raman scattered photons;
   detecting said Raman scattered photons using time-gated detection to thereby obtain a Raman spectroscopic image from the irradiated region for at least one Raman spectroscopic value characteristic of at least one of a neoplastic portion in said region containing the biological tissue and a non-neoplastic portion of said region containing the biological tissue, wherein said Raman spectroscopic image comprises spectral information recorded at each pixel in the image;
   differentiating a boundary between the neoplastic portion and the non-neoplastic portion in the region containing the biological tissue wherein said differentiating comprises analyzing said spectral information recorded at each pixel of said Raman spectroscopic image using a method selected from the group consisting of: principle component analysis, cosine correlation analysis, Euclidian distance analysis, multivariate curve resolution, band t. entropy method, mahalanobis distance, adaptive subspace detector, and combinations thereof; and
   displaying a location of said boundary in said Raman spectroscopic image.

2. The method of claim 1 further comprising selecting at least one of the neoplastic portion and the non-neoplastic portion for physical manipulation, wherein said selecting is based on the displayed boundary location between the neoplastic portion and the non-neoplastic portion.

3. The method of claim 2 further comprising physically manipulating at least one of the neoplastic portion and the non-neoplastic portion.

4. The method of claim 3 wherein the step of physically manipulating the neoplastic portion is performed in vivo on the region of biological tissue of a patient.

5. The method of claim 3 wherein physically manipulating the neoplastic portion comprises excising the neoplastic portion from the region containing said biological tissue.

6. The method of claim 5 wherein the steps of differentiating, selecting, and excising the selected neoplastic portion are performed iteratively.

7. The method of claim 5 wherein the steps of differentiating, selecting, and excising the selected neoplastic portion are performed iteratively and in vivo on the region of biological tissue of the patient.

8. The method of claim 5 further comprising rinsing the region containing biological tissue between the steps of selecting and excising.

9. The method of claim 8 wherein the step of rinsing the region containing biological tissue between the steps of selecting and excising is performed in vivo on the region of biological tissue of the patient.

10. The method of claim 3 wherein physically manipulating the neoplastic portion comprises at least one of the following: applying radioactive material to the neoplastic portion; applying heat to the neoplastic portion; applying electrical current to the neoplastic portion; applying a chemotherapy drug to the neoplastic portion; applying a gene therapy treatment to the neoplastic portion; and irradiating the neoplastic portion with radiation having a wavelength corresponding to a photoactivatable cytotoxic agent.

11. The method of claim 3 wherein the step of physically manipulating the neoplastic portion takes place in at least one of the following: a neurological operating room; a neurological procedure room; a radiology suite; and a medical practitioner's office.

12. The method of claim 11 wherein the step of physically manipulating the neoplastic portion is performed in vivo on a region of tissue of the patient.

13. The method of claim 1 wherein said boundary location is determined by analyzing said spectral information recorded at each pixel of said Raman spectroscopic image using a method selected from the group consisting of: principle component analysis, cosine correlation analysis, Euclidian distance analysis, multivariate curve resolution, band t. entropy method, mahalanobis distance, adaptive subspace detector, and combinations thereof.

14. The method of claim 1 wherein said differentiating includes correlating the Raman spectral image with a visible image of the region.

15. The method of claim 1 wherein said at least one Raman spectroscopic value includes a Raman shift for one of the following: the neoplastic portion and the non-neoplastic portion.

16. The method of claim 1 wherein said biological tissue comprises neurological tissue.

17. The method of claim 1 further comprising passing said Raman scattered photons through a tunable filter.

18. The method of claim 17 wherein said tunable filter is selected from the group consisting of: a liquid crystal tunable filter, a multi-conjugate tunable filter, an acousto-optic tunable filter, and combinations thereof.

19. A method comprising:
irradiating, with substantially monochromatic pulsed laser light, a region containing a neurological tissue to thereby produce Raman scattered photons;
detecting said Raman scattered photons using time-gated detection to thereby obtain Raman spectroscopic data from endogenous molecules in the irradiated region, wherein said Raman spectroscopic data comprises spatially resolved Raman spectroscopic data;
differentiating a boundary between a neoplastic portion and a non-neoplastic portion in the region containing the neurological tissue wherein
said differentiating comprises analyzing said spatially resolved Raman spectroscopic data in at least one direction for at least one Raman spectroscopic value characteristic of either endogenous molecules of the neoplastic portion or endogenous molecules of the non-neoplastic portion, and
wherein said analyzing comprises using a method selected from the group consisting of: principle component analysis, cosine correlation analysis, Euclidian distance analysis, multivariate curve resolution, band t. entropy method mahalanobis distance adaptive subspace detector, and combinations thereof.

20. The method of claim 19 further comprising selecting at least one of the neoplastic portion and the non-neoplastic portion wherein said selecting is based on the differentiation of the boundary between the neoplastic portion and the non-neoplastic portion.

21. The method of claim 20 further comprising physically manipulating at least one of: the neoplastic portion and the non-neoplastic portion.

22. The method of claim 21 wherein the step of physically manipulating the neoplastic portion is performed in vivo on the region of neurological tissue of a patient.

23. The method of claim 19 wherein said differentiating includes correlating the Raman spectral data with a visible image of the region.

24. The method of claim 19 further comprising, obtaining a Raman spectroscopic image from the irradiated region for at least one Raman spectroscopic value characteristic of at least one of: the neoplastic portion containing the neurological tissue and the non-neoplastic portion containing the neurological tissue.

25. The method of claim 19 further comprising passing said Raman scattered photons through a tunable filter.

26. The method of claim 25 wherein said tunable filter is selected from the group consisting of: a liquid crystal tunable filter, a multi-conjugate tunable filter, an acousto-optic tunable filter, and combinations thereof.

* * * * *